US008663670B1

(12) United States Patent
Kish

(10) Patent No.: US 8,663,670 B1
(45) Date of Patent: Mar. 4, 2014

(54) CONTROL OF BEDBUGS AND SO FORTH

(76) Inventor: William Kish, Wadsworth, OH (US)

( * ) Notice: Subject to any disclaimer, the term of this patent is extended or adjusted under 35 U.S.C. 154(b) by 0 days.

(21) Appl. No.: 13/385,670

(22) Filed: Feb. 29, 2012

Related U.S. Application Data

(60) Provisional application No. 61/464,236, filed on Mar. 1, 2011, provisional application No. 61/519,320, filed on May 20, 2011.

(51) Int. Cl.
| | |
|---|---|
| *A01N 25/00* | (2006.01) |
| *A61K 33/42* | (2006.01) |
| *A01N 59/26* | (2006.01) |
| *A01N 59/00* | (2006.01) |
| *A61K 33/02* | (2006.01) |

(52) U.S. Cl.
USPC .......................... 424/405; 424/601; 424/719

(58) Field of Classification Search
None
See application file for complete search history.

(56) References Cited

U.S. PATENT DOCUMENTS

| | | | | |
|---|---|---|---|---|
| 4,998,377 | A | 3/1991 | Tsutsumi | 43/125 |
| 6,288,010 | B1 * | 9/2001 | Rose et al. | 504/206 |
| 6,319,431 | B1 * | 11/2001 | Basson et al. | 252/607 |
| 2002/0129632 | A1 * | 9/2002 | Sheppardson et al. | 71/27 |
| 2007/0176156 | A1 * | 8/2007 | Mabey et al. | 252/601 |
| 2010/0028295 | A1 * | 2/2010 | Taranta et al. | 424/84 |

OTHER PUBLICATIONS

"Best Management Practices for Controlling Bed Bugs" obtained from www.nysipm.cornell.edu, Feb. 21, 2011.*
FoxNews.com "Superbug Germ Detected in Bedbugs, Study Finds," May 11, 2011 A.D., downloaded May 11, 2011, 1 page.
Commission on Life Sciences, The National Academics Press, "Toxicological Risks of Selected Flame Retardant Chemicals," pp. 274, 276, & 280; 2000 A.D., downloaded Dec. 2, 2011.
Wikipedia, Sodium Dodecyl Sulfate, Feb. 17, 2012, 5 pages, printed Feb. 28, 2012.
Hawley; The Condensed Chemical Dictionary, Tenth Edition, Van Nostrand Reinhold Company, 1981, pp. 62, 143, 563.
USPTO Patent Full-Text and Image Database, ACLM/"substantial amount," Hits 1 through 50 of 2866, Sep. 19, 2013.
USPTO Patent Full-Text and Image Database, ACLM/"minorl amount," Hits 1 through 50 of 4399, Sep. 19, 2013.
Anderson, eHow, "Bedbug Symptoms," www.ehow.com, 2 pages, printed Sep. 19, 2013.
Zhu et al., Scientific Reports 3, Article No. 1456, "Bed bugs evolved unique adaptave strategy to resist parathyroid insecticdes," recd. Dec. 28, 2012, publ. Mar. 14, 2013.

\* cited by examiner

*Primary Examiner* — Carlos Azpuru
*Assistant Examiner* — Casey Hagopian
(74) *Attorney, Agent, or Firm* — Christopher John Rudy

(57) ABSTRACT

Composition for control of insect pests includes an ammonium phosphate containing formulation effective for the kill and/or control of a hatched insect pest and/or an insect pest egg. Provided in a second aspect is a method for kill or control of an insect pest, which includes providing the composition; and applying it so as to contact an insect pest and/or an insect pest egg in an amount effective to kill or control the insect pest and/or insect pest egg. Protocol methodology for inspection of premises that may contain the insect pest and/or insect pest egg, and, if necessary, for kill or control of the same, which may include by employment of the method for control of the insect pest, is also provided. Bedbugs and/or their eggs are a special target effectively killed or controlled.

9 Claims, No Drawings

CONTROL OF BEDBUGS AND SO FORTH

This claims the benefits under 35 USC 119(e) of provisional patent application Nos. U.S. 61/464,236 filed on Mar. 1, 2011 A.D., and U.S. 61/519,320 filed on May 20, 2011 A.D. The specifications of those provisional patent applications are incorporated herein by reference in their entireties.

FIELD OF THE INVENTION

This concerns a composition and method to control insect pests, notably bedbugs.

BACKGROUND TO THE INVENTION

Among various insect pests, bedbugs are becoming more and more of a concern. This is especially so as commerce and traffic increase locally and globally.

For instance, hotels and motels can have a significant problem with bedbugs. The constant coming and going of guests, many of whom travel often, far and wide, and the ineffectiveness or inadequacy of compositions or methods for treatment contribute to this.

It would be desirable to provide generally safe and effective ways and means to ameliorate, if not completely control, insect pests, especially the scourge of bedbugs. It would be desirable to provide an alternative to the art.

A FULL DISCLOSURE OF THE INVENTION

In general, provided in one aspect is a composition for control of insect pests, which comprises an ammonium phosphate containing formulation effective for the kill and/or control of a hatched insect pest and/or an insect pest egg. Provided in a second aspect is a method for kill or control of an insect pest, which comprises providing the aforesaid composition; and applying the composition so as to contact an insect pest and/or an insect pest egg in an amount effective to kill or control the insect pest and/or insect pest egg. Protocol methodology for inspection of premises that may contain the insect pest and/or insect pest egg, and, if necessary, for kill or control of the same, which may include by employment of the method for control of the insect pest, is also provided.

The invention is useful in the kill or control of insect pests, especially bedbugs.

Significantly, by the invention, the art is advanced in kind, and an alternative is provided. A generally safe and effective composition is provided to ameliorate, if not completely control, insect pests, especially bedbugs. The method and protocol can be employed by many walks of people including staff at motels, hotels, and so on where in spite of high turnover good results can be achieved. The invention is economical and simple to make and use. Many further advantages attend the invention.

The invention can be further understood by its details. As with the foregoing, the following detail is to be taken in an illustrative and not necessarily limiting sense.

Included in the present composition is an ammonium phosphate. For instance, the ammonium phosphate may be a mono-ammonium phosphate, a di-ammonium phosphate, an ammonium polyphosphate, an ammonium orthophosphate, and so forth, or a combination thereof.

One or more additional ingredient(s) may be employed, which may include wetting and/or other agent(s) such as what may be considered to be surface tension lowering agent(s), cleaner(s), surfactant(s), defoaming agent(s), dispersing agent(s), thickening agent(s), preservative(s), which may be biocidal, fragrance(s) and so forth and the like. Thus may be employed, typically in minor amounts, a zwitterionic chemical compound with an alkylammonium cation as a defoamer or thickening agent such as coco amido-propyl betaine; a silicone defoamer, which may be of a silicone or silicone-modified mineral oil, say, Byk® 022 and/or 035 (BYK Chemie) or Foamstar® A10 and/or A12 block copolymer (Cognis Deutschland GmbH); an alkyl polyglycoside cleaner, which may include such a cleaner as one based on natural $C_{8-14}$ fatty alcohols, say, Glucopon® 425N cleaner (Cognis); a quaternary organic ammonium halide as a defoamer or even mold inhibitor, illustratively, a quaternary alkyl ammonium chloride, say, didecyldimethylammonium chloride, and/or a quaternary alkyl aromatic ammonium chloride, say, an alkyldimethylbenzylammonium chloride, for example, Maquat® CS428 alkyldimethylbenzylammonium chloride (80% aqueous solution) (Mason Chemical Co), which contains $C_{12-16}$alkyldimethylbenzylammonium chloride (CAS #68424-85-1) (80% by weight); ethanol (CAS #64-17-5) (10% by weight); and water (10% by weight); a preservative such as salicylic acid or a salicylate such as potassium salicylate; a suitable fragrance; and so forth and the like.

As additional ingredient(s) further to the aforementioned wetting and/or other agent(s) may be provided an anionic ionic surfactant/detergent such as a sulfonated aliphatic compound, to include a medium chain aliphatic or alkyl compound or mixture of aliphatic and/or alkyl compounds, for instance, provided or taken as a salt, say an alkali metal salt such as independently at each occurrence of lithium, sodium and/or potassium, which can enhance the insecticidal activity of the present composition. A medium chain can include, independently at each occurrence, about from five to twenty carbons, to include about from eight to sixteen carbons, for instance, about from ten to fourteen carbons, say, about twelve carbons. For example, the anionic ionic surfactant/detergent may be sodium lauryl sulfate, which can be a mixture of sodium alkyl sulfates consisting chiefly of sodium dodecyl sulfate, $C_{12}H_{25}NaO_4S$, and which may contain not less than 85% of sodium alkyl sulfates, calculated as $C_{12}H_{25}NaO_4S$. The anionic ionic surfactant/detergent may be provided in a diluent, for example, in water, at any suitable concentration such as about from 10 to 50 percent solids, to include about from 20 to 40 or about from 25 to 33 percent solids. When added to a formulation in a diluent, the mixture may be added in place of any diluent otherwise present.

A diluent may be employed. For example, water and/or other diluent may be employed to make a liquid composition. The composition may be provided without diluent, say, as a dry composition initially or after evaporation or sublimation of diluent. A dry or concentrated composition may be reconstituted or diluted with diluent.

Any suitable amount, proportion or concentration of ingredient(s) may be employed. For instance, a composition optionally with the ammonium phosphate and wetting and/or other agent(s) may be, independently at each occurrence, such as follows, with percentages by weight, which may be considered to be exact or approximate:

| | |
|---|---|
| Ammonium phosphate, e.g., mono- and/or di-ammonium phosphate(s), which may be an ammonium orthophosphate | 2~100%, 5~90%, 10~50%, 15~30% or 18~24% |
| Diluent, e.g., water | 0%, 10~98%, 50~95%, 70~85% or 75~80% |

-continued

| | |
|---|---|
| First wetting and/or other agent(s) | 0%, 0.01~10%, 0.1~5%, 0.5~2% or 1~1.5% |
| Anionic surfactant(s)/detergent(s) other than the first wetting and/or other agent(s) such as a sulfonated aliphatic salt(s), e.g., a mixture of sulfonated alkyl salts chiefly of sodium lauryl sulfate (sodium dodecyl sulfate), which can be added within a diluent, e.g., water | 0%, 0.1~10%, 0.3~8%, 0.5~5% or 0.7~2%. |

Particular first wetting and/or other agent(s) may be, independently at each occurrence, as follows, with percentages by weight, which may be considered as exact or approximate:

| | |
|---|---|
| Zwitterionic compound, e.g., coco amido-propyl betaine | 0%, 0.1~1% or 0.2~0.3% |
| Silicone defoamer, e.g., Foamstar® A10 | 0%, 0.1~1% or 0.15~0.3% |
| Alkyl polyglycoside cleaner, e.g., Glucopon® 425N | 0%, 0.1~5% or 0.4~0.7% |
| Quaternary organic ammonium halide, e.g., Maquat® CS428 | 0%, 0.1~1% or 0.2~0.3% |
| Preservative, e.g., salicylic acid | 0%, 0.01~0.1% or 0.03~0.05% |
| Fragrance, e.g., fruit or flower | 0%, 0.01~0.2% or 0.03~0.1%. |

An example of a particular anionic surfactant/detergent that can be employed to effect is sodium lauryl sulfate, for instance, as about 30% solids in water, say, at about from 3 to 5% of the formulation, for example, at or at about 4% by weight of the formulation so that there would be about 1.2% anionic surfactant detergent in the foregoing formulation. As mentioned, a corresponding amount of other diluent, say, water, is not added. Of course, the ingredient(s) together yield 100%. Thus, corresponding amounts based on a predetermined ingredient amount in the above general formulations may be determined.

Use of the composition includes applying the composition so as to contact an insect pest and/or an insect pest egg in an amount effective to kill or control the insect pest and/or insect pest egg. The application may be made directly to the insect pest and/or insect pest egg, or it may be made indirectly such as by applying the composition to a substrate, for example, bedding, which then contacts the insect pest and/or insect pest egg. Also, contact with the insect pest and/or insect pest egg plus the substrate may be made together, for example, when treating infested bedding with the composition. For example, the composition may be sprayed on materials such as the mattresses and their seams, couches, chairs, carpeting, suitcases and travel bags. Bedclothes and so forth also may be treated with the composition. As a liquid suitable for spraying, the liquid may be placed into any suitable container, for example, a spray bottle, which may be shaken for a suitable amount of time, say, fifteen seconds, before spraying. The spray bottle may be held a suitable distance from the material to be sprayed, say, about 6-10 inches or more depending on the configuration of the sprayer, and the material sprayed with the composition until all intended surfaces are saturated, for example, approximately seventy-five square feet per quart.

The insect pest or insect pest egg may be a bedbug or the egg of a bedbug.

The following examples and protocols further illustrate the invention.

EXAMPLE 1

A composition for control of insect pests was prepared by mixing in sequence ingredients such as follows:

| | |
|---|---|
| Water | 4.613 lbs. |
| Di-ammonium orthophosphate (40% aqueous) | 5.250 lbs. |
| Coco amidopropyl betaine | 0.025 lbs. |
| Foamstar® A10 block copolymer | 0.020 lbs. |
| Glucopon® 425N cleaner | 0.057 lbs. |
| Green apple fragrance | 0.006 lbs. |
| Salicylic acid | 0.004 lbs. |
| Maquat® CS428 defoamer | 0.025 lbs. |

The aqueous liquid composition is stored between 40-90° F.

EXAMPLE 2

A composition as of Example 1 was evaluated in a laboratory as follows:

As test insects, a field strain of the common bedbug (*Cimex lectularius*) maintained in the laboratory since 2009 was used for all experiments.

The bedbugs were held in a walk-in environmental chamber (26° C., 60% relative humidity, 12:12 light:dark cycle). Test arenas used were Pyrex® glass Petri dishes (9 cm by 1.5 cm). The composition and a control (water) were tested with ten replicates each. Each replicate contained ten insects (ten replicates times ten insects per replicate equaling one hundred insects per treatment). For each replicate, adult bedbugs (male and female) were used, and all insects were treated on the same day.

To directly treat the insects with either the composition or control, each replicate of ten insects was placed in a Petri dish and sprayed with a fine mist spray bottle. Each dish received four "pumps" from a spray bottle so that all ten insects in a dish were completely wetted. Immediately after being sprayed, the insects were transferred with forceps to new glass Petri dishes lined with filter paper (Whatman, grade No. 1) and held in the walk-in environmental chamber. Insect knockdown was recorded four hours after treatment, then daily for seven days. Data were analyzed statistically to look for significant differences between treatments with the composition and control.

At four hours after treatment, with the beginning of data collection, all insects sprayed with the composition were knocked down and no voluntary movement (walking) or involuntary movement (leg or antenna twitching) was observed. At that same time point, no knockdown was observed in the control group. Twenty-four hours after treatment, all insects in group treated with the composition remained knocked down (no body movement), and all insects in the control group were alive and moving normally. Mortality was checked each day for seven days, and no change was observed except that one control insect died four days after treatment. Mortality among insects that were knocked down was confirmed by observing hardening of the legs (legs no longer soft and pliable) and darkening of the body. Mortality in the experimental group treated with the composition was 100%, which was significantly higher than the 1% mortality observed in the control group (Fisher's Exact Test, $P<0.0001$). After the composition was applied and had dried, a white residue was observed on some treated insects.

To better understand more exactly how long it would take for bedbugs to stop moving after being sprayed with the composition, a follow-up experiment was carried out in which four replicates of ten adult bedbugs (male and female, forty insects total) were sprayed with the composition and observed to see how long after treatment all body movement stopped. The recorded times for all four groups ranged as follows:

| Insect Group | Time When Movement Stopped |
|---|---|
| No. 1 | 30 seconds |
| No. 2 | 11 minutes, 15 seconds |
| No. 3 | 4 minutes, 5 seconds |
| No. 4 | 41 seconds. |

EXAMPLES 3-5

A composition as of Example 1 was sprayed on separate samples of cockroaches, spiders, and silverfish. In each case, the pest sample was controlled with killing of pests.

Protocol 1

A procedure for an inspection of a guest room or other appropriate location in a hotel, motel, lodge, bed and breakfast establishment, college or retreat house dormitory, cruise ship, other establishment in the hospitality industry; a room or bay in a military barracks or camp, or quarters on ship; a pertinent room or area in a home, travel trailer, recreational vehicle, or private camp; and so forth and the like is set forth as follows:

If at any time evidence of bedbugs is found, stop the inspection and follow the established procedure for alerting management. A flashlight and a pry tool are needed.

1. Standing on either side of a bed, inspect any pillow cases, then any pillows as they are removed from the cases.
2. Beginning at the head of the bed, slowly remove any bed spread, inspecting the top and bottom seams on all sides. Pull corners toward the center of bed as one inspects.
3. Slowly remove any blanket, inspecting the edges, and pull corners to the center of the bed.
4. Slowly remove any upper sheet, inspecting the seams and edges, especially those tucked under the mattress, and pull corners to the center of bed.
5. Repeat the previous step with regard to any lower sheet, giving special attention to the corner seams of fitted sheets.
6. Lift and inspect pad seams and elastic strap connections, if present. Pull corners to the center of the bed. Bundle all bed dressing and remove from the bed.
7. Inspect any mattress seam (cord) on the top side and around all other sides of the mattress. Inspect all tags, labels or stickers.
8. Standing at the foot of the bed, lift the mattress and inspect any bottom seam (cord) at the foot of bed.
9. Slide the mattress off the foot of the bed, and stand it vertically at the foot of the bed.
10. Inspect the bottom side seam (cord) on the remaining three sides. Inspect all tags, labels or stickers. After inspection, place the mattress aside and out of the way.
11. Remove and very carefully inspect any dust ruffle, and carefully place it aside since dust ruffles for box springs go around the perimeter of the box spring.
12. Inspect the top seams and folds (at corners) of any box spring on all sides. Inspect all tags and labels.
13. If plastic corner caps are present on box springs, pry back slightly to inspect the area underneath each cap. Try to avoid causing loose staples.
14. If a headboard is removable, lift off its base and lay it face down on the box springs to inspect its backside. Pay close attention to any seams, gaps or screw holes. Place the headboard aside.
15. Inspect any gap behind a hanger for the headboard.
16. Return the headboard to the wall hanger.
17. Stand at the foot of the bed, and lift the box springs to inspect the bottom edge.
18. Lift the box spring from the frame, and stand it vertically at the foot of the bed. Inspect the remaining sides of the bottom edge. Place the box springs aside.
19. Inspect the bed frame, paying close attention to corners, gaps, seams, caps, and so forth and the like.
20. Inspect the baseboard area below the headboard.
21. Return the headboard.
22. Return the box springs on the frame, being very careful to not puncture any material on the box spring.
23. Return the dust ruffle, and then return the mattress.
24. Inspect all seams, creases, folds, legs, covers of any fabric chairs. Pay close attention to fabric covering the bottom of chairs. Inspect behind any buttons.
25. Inspect seams, edges, corners, and so forth and the like of any other furniture in the room.
26. Inspect any curtains, wall hangings, and so forth. Pay close attention to seams, gathered fabric such as pleats, and so forth.

Protocol 2

A procedure for full treatment of rooms or locations is set forth as follows:

The composition of Example 1 is provided. It is contained or packaged appropriately, for example, in a spray bottle having a nozzle with a mist adjustment from coarse to fine spray such as the Model No. 28-400 TS 800 from Continental AFA Dispersion Company, and should be shaken for fifteen seconds before use.

When treating, keep the spray nozzle within six to ten inches of the area being treated, using the coarse, not the fine, mist. The surface treated should be saturated. Avoid overspray. Begin the treatment sequence where the bed bugs were found so as to avoid scattering.

1. Carefully remove all bedding, and place each piece in a plastic bag as it is being removed. Do not put bedding from an infested room on the floor or on other furniture.
2. After all bedding has been removed from bed(s) and bagged, the bag should be tightly sealed and taken to a designated area such as in housekeeping.
3. Remove the headboard and lay it face down on the mattress. Treat all seams, gaps, screw holes, tags, labels or other harborage areas on the backside of the headboard.
4. Treat the headboard wall hanger, and treat the gap between it and the wall. Place the headboard aside and return it to the wall after post treatment inspection (noting step No. 19).
5. Treat all seams (cords), folds, labels on top side of the mattress.
6. Treat any handles or air holes on the sides of the mattress.
7. Standing at the foot of the bed, lift the mattress and treat the bottom seam (cord) of the mattress.
8. Slide the mattress off the foot of the bed, and then stand it vertically at the foot of the bed.

9. Treat the bottom seam (cord) on the remaining three sides, being cautious of overspray. Place the treated mattress aside and out of the way to return after post treatment inspection (noting step No. 19).
10. Treat the top side of any box springs, paying close attention to all seams, folds, labels, etc. Treat in the folds at the corners of the box spring.
11. If plastic corner caps are present, pry them back slightly, and treat under each cap.
12. Standing at the foot of the bed, lift the box spring, and treat its bottom seam.
13. Lift the box spring from the frame, and stand it vertically at the foot of the bed. Treat the remaining sides of the bottom of the box spring. It is very important to thoroughly treat the stapled edge of the fabric covering the bottom of the box springs if it is present. If it is not, treat the interior of the box springs as much as possible including the seams between wooden cross members. Place treated box spring aside and out of the way to return after post treatment inspection (noting step No. 19).
14. Do not return the mattress and box springs until post treatment inspection is complete (noting step No. 19).
15. Treat the baseboard around the room, making sure to treat the seam between the floor, wall and all corners. If the baseboard has pulled away from the wall, treat the area behind the baseboard.
16. Treat all seams, creases, folds, and legs of fabric chairs, especially the edges of the material covering the bottom of the chair. Treat behind any buttons.
17. Inspect all other furniture. If bed bugs or eggs are found, treat the cracks, seams, gaps, and so forth and the like of those pieces, being careful to not overspray or create excessive runoff.
18. Treat curtains and wall hangings as necessary by spraying, or carefully remove.
19. Three to four hours after treatment, inspect the room or location to find any dead or dying stragglers, and remove them. Reassemble the room or location.

EXAMPLE 6

A composition such as of Example 1 has 4% by weight sodium lauryl sulfate (28.95% solids in water) added in place of a corresponding amount of plain water. The mixture is thus enhanced, and can kill or control bedbugs and their eggs to effect. The effect is even more pronounced than that illustrated by Example 2 or Examples 3-5. Also, methodology such as the methodology set forth in Protocols 1 and 2 may be employed to effect with this composition.

CONCLUSION TO THE INVENTION

The instant invention is thus provided. Various feature(s), part(s), step(s), subcombination(s) and/or combination(s) can be employed with or without reference to other feature(s), part(s), step(s), subcombination(s) and/or combination(s) in the practice of the invention, and numerous and sundry adaptations and modifications can be effected within its spirit, the literal claim scope of which is particularly pointed out as follows:

What is claimed is:
1. A method for killing a hatched bedbug and/or a bedbug egg, which comprises carrying out the following steps:
   inspecting for a presence of the hatched bedbug and/or the bedbug egg;
   providing a liquid composition of a formulation effective for the kill of a hatched bedbug and a bedbug egg, wherein the formulation has an ammonium phosphate, a diluent with water, and at least one agent selected from the group consisting of an organic wetting agent, a silicone wetting agent, and another agent selected from the group consisting of
   cleaner(s),
   surfactant(s),
   defoaming agent(s),
   dispersing agent(s),
   thickening agent(s),
   preservative(s),
   fragrance(s), and
   a combination whereof; and
   wherein the formulation is one selected from the group consisting of a first formulation, with percentages by weight, approximately as follows:
      Ammonium phosphate including mono- and/or di-ammonium phosphate(s) 15~30%
      Water 70~85%
      Wetting and/or other agents) 0.5~2%, and
   a second formulation, with percentages by weight, approximately as follows:
      Ammonium phosphate including mono- and/or di-ammonium phosphate(s) 15~30%
      Water 70~85%
      First wetting 0.5~2%
      Anionic surfactant(s)/detergent(s) other than the first wetting and/or other agents 0.5~5%;
   and the composition is such that—when evaluated in a laboratory with a field strain of common bedbug (*Cimex lectularius*) as follows:
      with the bedbugs being held in a walk-in environmental chamber at 26° C., 60% relative humidity, 12:12 light:dark cycle; with test arenas being glass Petri dishes (9 cm by 1.5 cm); with the composition being tested with ten replicates each, with each replicate containing ten bedbugs (ten replicates times ten bedbugs per replicate equaling one hundred bedbugs per treatment) and, for each replicate, adult male and female bedbugs being used, and all bedbugs being treated on the same day; with the bedbugs being directly treated with the composition, each replicate of ten bedbugs being placed in one of the glass Petri dishes and sprayed with a fine mist spray bottle; with each glass Petri dish receiving four pumps from a spray bottle so that all ten bedbugs in the dish are completely wetted; with the bedbugs, immediately after being sprayed, being transferred with forceps to new glass Petri dishes lined with filter paper and being held in the walk-in environmental chamber; and
      with bedbug observation being recorded four hours after treatment, then daily for seven days—
   the following is observed:
      at four hours after treatment, with the beginning of data collection, all bedbugs sprayed with the composition exhibit no voluntary body movement (walking) or involuntary body movement (leg or antenna twitching);
      at twenty-four hours after treatment, all bedbugs in the group treated with the composition exhibit no body movement; and
      with mortality being checked each day for seven days, and no change in body movement being observed, the mortality is 100%; and applying the composition so as to contact the hatched bedbug and/or the bedbug egg in a safe and effective amount to kill the hatched bedbug and/or the bedbug egg—wherein at least one of inspection protocol methodology and full treatment protocol methodology is employed, wherein the inspection protocol methodology employs a flashlight and a pry tool as needed, with employment of the following steps (A-Z);

(A) standing on either side of a bed, inspecting any pillow cases, any pillows they are removed the cases;

(B) beginning at a head of the bed, slowly removing any bed spread, bottom seams on all pulling corners toward a center of bed;

(C) slowly removing any blanket, inspecting the edges, and pulling corners to the center of the bed;

(D) slowly removing any upper sheet, inspecting the seams and edges, especially those tucked under a mattress, and pulling corners to the center of the bed;

(E) repeating step D with regard to any lower sheet, giving special attention to corner seams of fitted sheets;

(F) lifting and inspecting pad seams and elastic strap connections, if present, pulling corners to the center of the bed; bundling all bed dressing and removing from the bed;

(G) inspecting any mattress seam (cord) on a top side and around all other sides of the mattress; inspecting all tags, labels or stickers;

(H) standing at the foot of the bed, lifting the mattress and inspecting any bottom seam (cord) at a foot of bed;

(I) sliding mattress off the foot of the bed, and standing it vertically at the foot of the bed;

(J) inspecting the bottom side seam (cord) on remaining sides of the mattress, inspecting all tags, labels or stickers; after inspection, placing the mattress aside and out of the way;

(K) removing and very carefully inspecting any dust ruffle around a perimeter of any box spring, and carefully placing it aside;

(L) inspecting top seams and folds (at corners) of any box spring on all sides, inspecting all tags and labels;

(M) if plastic corner caps are present on box springs, prying back slightly to inspect underneath each cap, trying to avoid causing loose staples;

(N) if a headboard is removable, lifting off its base and laying it face down on the box springs to inspect its backside, paying close attention to any seams, gaps or screw holes; placing the headboard aside;

(O) inspecting any gap behind a hanger for the headboard;

(P) returning the headboard to the wall hanger;

(Q) standing at the foot of the bed, lifting the box springs to inspect a bottom edge;

(R) lifting the box springs from a bed frame, and standing the box springs vertically at the foot of the bed; inspecting remaining sides of the bottom edge, and placing the box springs aside;

(S) inspecting the bed frame, paying close attention to corners, gaps, seams and caps;

(T) inspecting baseboard area below the headboard;

(U) returning the headboard;

(V) returning the box springs on the frame, being very careful to not puncture any material on the box spring;

(W) returning the dust ruffle, and then returning the mattress;

(X) inspecting all seams, creases, folds, legs and covers of any fabric chairs, paying close attention to fabric covering bottoms of chairs, inspecting behind any buttons;

(Y) inspecting seams, edges and corners of any other furniture in the room; and (Z) inspecting any curtains and wall hangings, paying close attention to seams and gathered fabric;

and the full treatment protocol methodology, when treating, saturates a surface treated through spraying, and begins a treatment sequence where bedbugs are found so as to avoid scattering, with employment of the following steps (A'-T');

(A') carefully removing all bedding, and placing each piece in a plastic bag as it is being removed, not putting bedding from an infested room on a floor or on other furniture;

(B') after all bedding is removed from bed(s) and bagged in a bag, tightly sealing the bag and taking it to a designated area;

(C') removing any headboard and laying it face down on a mattress, treating all seams, gaps, screw holes, tags, labels or other harborage areas on a backside of the headboard;

(D') treating a headboard wall hanger on a wall, and treating any gap between it and the wall; placing the headboard aside and returning it to the wall after post treatment inspection (step "S'");

(E') treating all seams (cords), folds, labels on a top side of the mattress;

(F') treating any handles or air holes on sides of the mattress;

(G') standing at a foot of the bed, lifting the mattress and treating a bottom seam (cord) of the mattress;

(H') sliding the mattress the foot of the bed, and then standing it vertically at the foot of the bed;

(I') treating the bottom seam (cord) on remaining sides, being cautious of overspraying; placing the treated mattress aside and out of the way to return after post treatment inspection (step "S'"):

(J') treating a top side of any box springs, paying close attention to all seams, folds and labels; treating in any folds at corners of the box spring;

(K') if plastic corner caps are present, prying them back slightly, and treating under each cap;

(L') standing at the foot of the bed, lifting the box spring, and treating its bottom seam;

(M') lifting the box spring from a bed frame, and standing it vertically at the foot of the bed; treating remaining sides of the bottom of the box spring, thoroughly treating any stapled edge of fabric covering the bottom of the box springs if present, but, if not, treating the interior of the box springs as much as possible including seams between wooden cross members; placing treated box spring aside and out of the way to turn after post treatment inspection (step "S'");

(N') not returning the mattress and box springs until post treatment inspection is complete (step "S'");

(O') treating baseboard around room, making sure to treat seams between the floor, wall and all corners; if the baseboard has pulled away from the wall, treating area behind the baseboard;

(P') treating all seams, creases, folds, and legs of fabric chairs, especially edges of material covering bottoms of the chairs, treating behind any buttons;

(Q') inspecting all other furniture; if bed bugs or bed bug eggs are found, treating cracks, seams and gaps of those pieces, being careful to not overspray or create excessive runoff;

(R') treating curtains and wall hangings as necessary by spraying, or carefully removing; and (S') three to four hours after treatment, inspecting the room or location to find any dead or dying stragglers, and removing them; and (T') reassembling the room or location.

2. The method of claim 1, wherein the formulation is the first formulation.

3. The method of claim 2, wherein both the inspection protocol methodology and the full treatment protocol methodology are employed.

4. The method of claim 1, wherein the formulation is the second formulation.

5. The method of claim 4, wherein both the inspection protocol methodology and the full treatment protocol methodology are employed.

6. A method for killing a hatched bedbug and/or a bedbug egg, which comprises carrying out the following steps:

inspecting for a presence of the hatched bedbug and/or the bedbug egg;

providing a liquid composition effective for the kill of a hatched bedbug and/or a bedbug egg, wherein the composition approximately is or in is proportion to the following:

Water 4.613 lbs.,

Di-ammonium orthophosphate (40% aqueous) 5.250 lbs.,

Coco amidopropyl betaine 0.025 lbs.,

Block copolymer silicone defoamer 0.020 lbs.,

Alkyl polyglycoside cleaner 0.057 lbs.,

Optional fruit or flower fragrance 0 or 0.006 lbs.,

Salicylic acid 0.004 lbs., and

Quaternary organic ammonium halide defoamer 0.025 lbs;

and the composition is such that—when evaluated in a laboratory with a field strain of common bedbug (*Cimex lectularius*) as follows:

with the bedbugs being held in a walk-in environmental chamber at 26° C. 60% relative humidity, 12:12 light: dark cycle: with test arenas being glass Petri dishes (9 cm by 1.5 cm): with the composition being tested with ten replicates each, with each replicate containing ten bedbugs (ten replicates times ten bedbugs per replicate equaling one hundred bedbugs per treatment) and, for each replicate, adult male and female bedbugs being used, and all bedbugs being treated on the same day; with the bedbugs being directly treated with the composition, placed in one of the glass Petri dishes and sprayed with a fine mist spray bottle; with each glass Petri dish receiving four pumps from a spray bottle so that all ten bedbugs in the dish are completely wetted; with the bedbugs, immediately after being sprayed, being transferred with forceps to new glass Petri dishes lined with filter paper and being held in the walk-in environmental chamber; and with bedbug observation being recorded four hours after treatment, then daily for seven days— the following is observed;

at four hours after treatment, with the beginning of data collection, all bedbugs sprayed with the composition exhibit no voluntary body movement (walking) or involuntary body movement (leg or antenna twitching);

at twenty-four hours after treatment, all bedbugs in the group treated with the composition exhibit no body movement; and with mortality being checked each day for seven days, and no change in body movement being observed, the mortality is 100%; and applying the composition so as to contact the hatched bedbug and/or the bedbug egg in a safe and effective amount to kill the hatched bedbug and/or the bedbug egg— wherein at least one of inspection protocol methodology and full treatment protocol methodology is employed, wherein the inspection protocol methodology employs a flashlight and a pry tool as needed, with employment of the following steps (A-Z):

(A) standing on either side of a bed, inspecting any pillow cases, then any pillows as they are removed from the cases;

(B) beginning at a head of the bed, slowly removing any bed spread, inspecting the top and bottom seams on all sides, pulling corners toward a center of bed;

(C) slowly removing any blanket, inspecting the edges, and pulling corners to the center of the bed;

(D) slowly removing any upper sheet, inspecting the seams and edges, especially those tucked under a mattress, and pulling corners to the center of the bed;

(E) repeating step D with regard to any lower sheet, giving special attention to corner seams of fitted sheets;

(F) lifting and inspecting pad seams and elastic strap connections, if present, pulling corners to the center of the bed; bundling all bed dressing and removing from the bed;

(G) inspecting any mattress seam (cord) on a top side and around all other sides of the mattress; inspecting all tags, labels or stickers;

(H) standing at the foot of the bed, lifting the mattress and inspecting any bottom seam (cord) at a foot of bed;

(I) sliding the mattress off the foot of the bed, and standing it vertically at the foot of the bed;

(J) inspecting the bottom side seam (cord) on remaining sides of the mattress, inspecting all tags, labels or stickers; after inspection, placing the mattress aside and out of the way;

(K) removing and very carefully inspecting any dust ruffle around a perimeter of any box spring, and carefully placing it aside;

(L) inspecting top seams and folds (at corners) of any box spring on all sides, inspecting all tags and labels;

(M) if plastic corner caps are present on box springs, prying back slightly to inspect area underneath each cap, trying to avoid causing loose staples;

(N) if a headboard is removable, lifting off its base and laying it face down on the box springs to inspect its backside, paying close attention to any seams, gaps or screw holes; placing the headboard aside;

(O) inspecting any gap behind a hanger for the headboard;

(P) returning the headboard to the wall hanger;

(Q) standing at the foot of the bed, lifting the box springs to inspect a bottom edge;

(R) lifting the box springs from a bed frame, and standing the box springs vertically at the foot of the bed; inspecting remaining sides of the bottom edge, and placing the box springs aside;

(S) inspecting the bed frame, paying close attention to corners, gaps, seams and caps;

(T) inspecting baseboard area below the headboard;
(U) returning the headboard;
(V) returning the box springs on the frame, being very careful to not puncture any material on the box spring;
(W) returning the dust ruffle, and then returning the mattress;
(X) inspecting all seams, creases, folds, legs and covers of any fabric chairs, paying close attention to fabric covering bottoms buttons;
(Y) inspecting seams edges and corners of any other furniture in the room; and
(Z) inspecting any curtains and wall hangings, paying close attention to seams and gathered fabric;

and the full treatment protocol methodology, when treating, saturates a surface treated through spraying, and begins a treatment sequence where bedbugs are found so as to avoids tittering, with employment of the following steps (A'-T'):

(A') carefully removing all bedding, and placing each piece in a plastic bag as it is being removed, not putting bedding from an infested room on a floor or on other furniture;
(B') after all bedding is removed from bed(s) and bagged in a bag, tightly sealing the bag and taking it to a designated area;
(C') removing any headboard and laying it face down on a mattress, treating all seams, gaps, screw holes, tags, labels or other harborage areas on a backside of the headboard;
(D') treating a headboard wall hanger on a wall, and treating any gap between it and the wall; placing the headboard aside and returning it to the wall afterpost treatment inspection (step "S'");
(E') treating all seams (cords), folds, labels on a top side of the mattress;
(F') treating any handles or air holes on sides of the mattress;
(G') standing at a foot of the bed, lifting the mattress and treating a bottom seam (cord) of the mattress;
(H') sliding the mattress off the foot of the bed, and then standing it vertically at the foot of the bed;
(I') treating the bottom seam (cord) on remaining sides, being cautious of overspraying; placing the treated mattress aside and out of the way to return after post treatment inspection (step "S'");
(J') treating a top side of any box springs, paying close attention to all seams, folds and labels; treating in any folds at corners of the box spring;
(K') if plastic corner caps are present, prying them back slightly, and treating under each cap;
(L') standing at the foot of the bed, lifting the box spring, and treating its bottom seam;
(M') lifting the box spring from a bed frame, and standing it vertically at the foot of the bed; treating remaining sides of the bottom of the box spring, thoroughly treating any stapled edge of fabric covering the bottom of the box springs if present, but, if not, treating the interior of the box springs as much as possible including seams between wooden cross members; placing treated box spring aside and out of the way to return after post treatment inspection (step "S'");
(N') not returning the mattress and box springs until post treatment inspection is complete (step "S'");
(O') treating baseboard around room, making sure to treat seams between the floor, wall and all corners; if the baseboard has pulled away from the wall, treating area behind the baseboard;
(P') treating all seams, creases, folds, and legs of fabric chairs especially edges of material covering bottoms of the chairs, treating behind any buttons;
(Q') inspecting all other furniture; if bed bugs or bed bug eggs are found, treating cracks, seams and gaps of those pieces, being careful to not overspray or create excessive runoff;
(R') treating curtains and wall hangings as necessary by spraying, or carefully removing; and
(S') three to four hours after treatment, inspecting the room or location to find any dead or dying stragglers, and removing them; and
(T') reassembling the room or location.

7. The method of claim 6, wherein both the inspection protocol methodology and the full treatment protocol methodology, are employed.

8. The method of claim 6, wherein about 4% by weight sodium lauryl sulfate (28.95% solids in water) is present in place of a corresponding amount of the water.

9. The method of claim 7, wherein about 4% by weight sodium lauryl sulfate (28.95% solids in water) is present in place of a corresponding amount of the water.

\* \* \* \* \*